US008426199B2

(12) United States Patent
Zimmermann et al.

(10) Patent No.: US 8,426,199 B2
(45) Date of Patent: Apr. 23, 2013

(54) METHOD FOR THE TREATMENT OF BIOLOGICAL TISSUE OF ANIMAL OR HUMAN ORIGIN, SUCH AS PORCINE, BOVINE PERICARDIUM OR HUMAN CADAVER HEART VALVES, AND BIOLOGICAL TISSUE TREATED ACCORDINGLY

(75) Inventors: Hanngörg Zimmermann, Göβweinstein (DE); Markus Heinlein, Göβweinstein (DE)

(73) Assignee: GfE Nanomedical International AG, La Chaux-de-Fonds (CH)

( * ) Notice: Subject to any disclaimer, the term of this patent is extended or adjusted under 35 U.S.C. 154(b) by 484 days.

(21) Appl. No.: 12/528,200

(22) PCT Filed: Jan. 11, 2008

(86) PCT No.: PCT/EP2008/000155
§ 371 (c)(1),
(2), (4) Date: Aug. 21, 2009

(87) PCT Pub. No.: WO2008/101566
PCT Pub. Date: Aug. 28, 2008

(65) Prior Publication Data
US 2010/0317080 A1 Dec. 16, 2010

(30) Foreign Application Priority Data
Feb. 24, 2007  (DE) .......................... 10 2007 009 095

(51) Int. Cl.
*C12N 5/071* (2010.01)
*C12N 5/02* (2006.01)
*A61F 2/06* (2006.01)
*A61F 2/08* (2006.01)

(52) U.S. Cl.
USPC ........... 435/366; 435/325; 623/2.1; 623/2.13; 623/2.14; 623/2.15; 623/2.16; 623/13.17

(58) Field of Classification Search ............ 623/2.1, 623/2.13, 2.14, 2.15, 2.16, 13.17; 435/325, 435/366
See application file for complete search history.

(56) References Cited

U.S. PATENT DOCUMENTS

| 6,057,031 A * | 5/2000 | Breme et al. ............... 428/336 |
| 2003/0170214 A1* | 9/2003 | Bader ..................... 424/93.21 |
| 2005/0223992 A1* | 10/2005 | Asmussen et al. .... 118/723 MW |
| 2006/0189976 A1* | 8/2006 | Karni et al. ................. 606/41 |

FOREIGN PATENT DOCUMENTS

| EP | 0 897 997 B1 | 2/1999 |
| EP | 1 286 708 B1 | 3/2003 |
| EP | 1 452 150 A1 | 9/2004 |
| EP | 1452150 A1 * | 9/2004 |
| WO | WO 01/91820 | 12/2001 |
| WO | WO 03/075790 A2 | 9/2003 |
| WO | WO 2005020847 A2 * | 3/2005 |
| WO | WO 2006/077582 A2 | 8/2006 |
| WO | WO 2006/116776 A2 | 11/2006 |
| WO | WO 2007/016122 A2 | 2/2007 |

OTHER PUBLICATIONS

Gott J.P., Chih P., Dorsey L., Jay J.L., Jett G.K., Schoen F.J., Girardot J.M., Guyton R.A. "Calcification of porcine valves: a successful new method of antimineralisation" in Ann Thorac Surg 1992; 53: 207-216.
Jones M., Eidbo E.E., Hilbert S.L., Ferrans V.J., Clarck R.E., "Anticalcification treatments of bioprosthetic heart valves: in vivo studies in sheep" in J Cardiovasc Surg 1989; 4: 69-73.
Grabenwöger M., Sider J., Fitzal F., Zelenka C., Windberger U., Grimm M. "Impact of glutaraldehyde on calcification of pericardial bioprosthetic heart valve material" in Ann Thorac Surg 1996; 62: 772-7.
Webb C.L., Benedict J.J., Schoen F.J., Linden J.A., Levy R.J., "Inhibition of bioprosthetic valve calcification with aminodiphosphonate covalently bound material to residual aldehyde groups" in Ann thorac Surg 1988; 46: 309-16.
Gulbins H., Goldemund A., Anderson I., Haas U., Uhlig A., Meiser B., Reichart B. "Preseeding with autologous fibroblasts improves endothelialisation of glutaraldehyde-fixed porcine aortic valves" in J Thorac Cardiovasc Surg 2003; 125: 592-601.

* cited by examiner

*Primary Examiner* — Blaine Lankford
*Assistant Examiner* — Charles Zoltan Constantine
(74) *Attorney, Agent, or Firm* — McGlew and Tuttle, P.C.

(57) ABSTRACT

A method for treating glutardialdehyde-stabilized biological tissue of animal or human origin, such as porcine, bovine pericardium or human cadaver heart valves, provides a physical plasma treatment of the, in particular, collagen tissue for increasing the biocompatibility, cell colonization and durability thereof.

14 Claims, No Drawings

METHOD FOR THE TREATMENT OF BIOLOGICAL TISSUE OF ANIMAL OR HUMAN ORIGIN, SUCH AS PORCINE, BOVINE PERICARDIUM OR HUMAN CADAVER HEART VALVES, AND BIOLOGICAL TISSUE TREATED ACCORDINGLY

BACKGROUND OF THE INVENTION

1. Field of the Invention

The invention relates to a method for the treatment of biological tissue of animal and human origin, such as porcine heart valves, heart valves of bovine pericardium or human cadaver heart valves, and biological tissue treated accordingly.

2. Background Art

With regard to the background of the invention it is to be stated that operation methods with an application of differently pre-treated biological tissue of animal origin, as collagen matrices, in particular in the course of tissue engineering, are gaining in importance in various surgical areas for future, improved therapy methods. Relevant application areas are to be seen in cardiovascular surgery, but orthopaedics and neurosurgery are also conceivable as areas of use.

For the application of collagen matrices in cardiovascular surgery, good blood compatibility and mechanical stability have to be ensured. As an example, in this context, heart valves of animal origin, such as porcine valves or valves of bovine pericardium are to be mentioned just as much as biological vessel prostheses with small diameters and pump chambers of biological or mechanical blood pumps. In orthopaedic surgical treatments, stable collagen matrices especially are of particular interest for the replacement of cartilage, ligaments and tendons. In neurosurgery, finally, a collagen tissue for closing the cranium, for example after tumour operations is to be regarded as an area of use of the present invention.

The special problems, on which the invention is based, are to be made clear from the example of replacement heart valves. Thus of the replacement heart valves implanted in over 200,000 patients a year worldwide about 50% are made from artificial, mechanical heart valves and 50% from biological implants based on porcine heart valves and valves from bovine pericardium. The implantation of mechanical heart valves, for permanent after-care, requires the administration of blood clotting-inhibiting medications, to avoid embolisms coming from the prostheses. Thus, patients attended to in this manner become virtually "artificial haemophiliacs".

Biological heart valves of animal origin have the problem that they have to be treated with glutaraldehyde to achieve long-term stability. Owing to the free aldehyde groups thus being produced from glutardialdehyde, the biological heart valves have a toxic effect per se and can therefore not be colonised with cells. A cell colonisation should make these biovalves durable for significantly longer. However, a detoxification would be necessary before a cell colonisation. Medical studies are known in this context from the prior art, in which substances are used which bind free aldehyde groups. Reference is made in this context to the following literature references:

Gott J. P., Chih P., Dorsey L., Jay J. L., Jett G. K., Schoen F. J., Girardot J. M., Guyton R. A. "Calcification of porcine valves: a successful new method of antimineralisation" in Ann Thorac Surg 1992; 53: 207-216; Jones M., Eidbo E. E., Hilbert S. L., Ferrans V. J., Clarck R. E. "Anticalcification treatments of bioprosthetic heart valves: in vivo studies in sheep" in J Cardiovasc Surg 1989; 4: 69-73; Grabenwöger M., Sider J., Fitzal F., Zelenka C., Windberger U., Grimm M. "Impact of glutaraldehyde on calcification of pericardial bioprosthetic heart valve material" in Ann Thorac Surg 1996; 62: 772-7 and finally Webb C. L., Benedict J. J., Schoen F. J., Linden J. A., Levy R. J. "Inhibition of bioprosthetic valve calcification with aminodiphosphonate covalently bound material to residual aldehyde groups" in Ann Thorac Surg 1988; 46: 309-16.

Furthermore, tests were carried out to achieve a detoxification with the aid of citric acid. This was partially successful as disclosed in Gulbins H., Goldemund A., Anderson I., Haas U., Uhlig A., Meiser B., Reichart B. "Preseeding with autologous fibroblasts improves endothelialisation of glutaraldehyde-fixed porcine aortic valves" in J Thorac Cardiovasc Surg 2003; 125: 592-601.

The degrees of detoxification achieved there were merely 20 to 30%.

With a suitable detoxification of the tissue fixed with glutaraldehyde and corresponding coatability by the body's own tissue after the implantation—so-called "endothelialisation"—it was possible to achieve the goal of a heart valve which could last for life without the administration of medications to inhibit blood clotting.

A further example of the scope of the present invention is small-bore vessel prostheses. Implants of this type are generally currently made of plastics material, namely PTFE or PET. They have a comparatively high closure rate, in particular in their application as a vessel replacement for peripheral leg vessels, aortocoronary bypasses and peripheral dialysis shunts. The consequences of vessel closures in these prosthesis regions are drastic, including leg amputation, myocardial infarction resulting in death or the necessity of a shunt revision. Here, too, small-bore glutaraldehyde-fixed biological tissue of animal origin in the form of porcine, bovine or goat donor vessels could bring a substantial improvement if tissue of this type could be detoxified and endothelialised, or is endothelialised in the bloodstream. In the application of muscular pumps, as well, thromboembolism complications could be avoided if the components coming into contact with the blood could be increased with regard to their biocompatibility, for example through suitable detoxification measures.

Further application areas of biological tissue of this type in the form of collagen matrices of animal origin may be stable and biocompatible glutaraldehyde-fixed and detoxified biological tissue for the treatment of osteoarthritis of the hip, knee and ankle joints. Furthermore, further applications to close the cranium after injuries or tumour operations with the aid of a correspondingly glutaraldehyde-fixed and detoxified bovine pericardium as a cerebro-protective application are just as conceivable as applications, for example, in thorax surgery as the thorax wall or diaphragm replacement, in abdominal surgery for abdominal wall replacement or in the ENT area as an eardrum replacement.

SUMMARY OF THE INVENTION

With regard to the problems outlined of the prior art, the invention is based on the object of disclosing a method for treating collagen tissue of animal or human origin and a correspondingly treated biological tissue, the biocompatibility and the long-term stability of the tissue being increased in such a way that the time of use of the tissue in the body can be drastically increased—in the optimal case up to capacity for permanent use.

The basic concept of the invention provides a physical plasma treatment of the biological tissue to solve these problems.

Tests have shown that owing to this physical plasma treatment, in which the gases used are excited and radicalised and which chemically neutralises the toxicity because of the free aldehyde groups produced because of the glutaraldehyde fixing, a significantly improved detoxification can therefore be achieved compared to the prior art as a first step for improving the implantation properties of the tissue. The tests mentioned have produced a degree of detoxification of over 80%. A closed endothelium surface could thus be colonised on the blood contact faces of the test tissue.

The chemical process basically proceeding during the plasma treatment can be briefly outlined using the example of the process gas oxygen. Thus the components present in the plasma, namely oxygen ions and the excited oxygen form carbon dioxide and water in the reaction with hydrocarbons on the tissue surface. This reaction can thus be used to remove the aldehyde groups present on the tissue surfaces, such as are produced through glutaraldehyde fixing, in the sense of a detoxification.

Preferred method conditions for the plasma gas method used are given, in which oxygen is preferably used as the excited gas. Nitrogen, hydrogen and argon may, however, also be used. The energy input for the production of the plasma, is advantageously implemented by a high-frequency electromagnetic field, in particular a microwave field.

The above plasma gas methods generally take place by the introduction of the gas to be ionised into an evacuated treatment chamber. In addition, it is also possible to carry out the plasma treatment with an atmospheric plasma using a plasma jet with excited reaction gas under atmospheric conditions. The plasma jet is guided over the implant surface, so local purification takes place. This takes place in that the oxygen ions present in the reaction gas undergo a reaction with hydrocarbons and the tissue surface and form carbon dioxide and water.

While, in the plasma treatment under atmospheric conditions, a preconditioning in the form of a drying of the tissue is no longer necessary, and therefore even moist tissue in its original state can be directly treated, for the treatment of the biological tissue with the plasma gas method mentioned at the outset in a treatment chamber, it is very advantageous for the detoxification result if the generally aqueous biological tissues are subjected before the plasma treatment to a drying, in particular by the influence of a vacuum and temperature.

The biological tissue is therefore kept completely water-free for the duration of the treatment.

Moisture is supplied to the tissue subjected to the plasma treatment for implantation use, in that it is placed in liquid, for example. It thus regains its original consistency and is, for example, permanently resilient and stable in the long-term in a corresponding implementation as a porcine heart valve.

In a particularly preferred development of the method according to the invention the tissue subject to the plasma treatment is provided with a biocompatible, metal-containing coating. This coating is an additional biocompatible component on the implant surfaces, which lastingly promotes the cell growth.

The method of choice for implementing the metal-containing coating is a PACVD method, which, in the coating of plastics material surfaces in artificial medical implants, has already achieved convincing results with regard to the biocompatibility of the surfaces treated therewith. This metal-containing coating is selected from the group of metals consisting of Ti, Ta, Nb, Zr, Hf, Ir, Au, Pd, Pt, Ag and Cu. In this context, titanium has proven particularly successful and has been used for a long time as a particularly biocompatible material in many types of implant applications. The coating materials also mentioned, silver and copper, may additionally or exclusively be introduced into the coating as antibacterial reagents.

Further preferred embodiments of the invention relate to biological tissue of animal or human origin, such as can be used as an implant in a human or animal body. According to the present invention, at least the surface which can be brought into contact with the body, is subjected to a plasma treatment according to the invention for detoxification. The biocompatibility is improved—as described above—by a biocompatible, metal-containing coating on the biological tissue. The biological tissue is preferably a heart valve, vessel prosthesis, blood contact face of mechanical or biomechanical blood pumps, closure insert for cranium openings, cartilage, bone, tendon, diaphragm, thorax wall, abdominal wall or eardrum replacement.

DESCRIPTION OF THE PREFERRED EMBODIMENTS

The following description describes the invention more closely in an embodiment:

A porcine heart valve is used as an example of a collagen tissue of animal origin, which is to be used as an implant in a human body.

This is prepared, de-cellularised and glutaraldehyde-fixed after removal from the donor animal for stabilisation in a conventional manner. In this case, the valve is brought into a glutaraldehyde solution of between 0.1 and 0.4% and fixed in a flowing solution at low pressures of 3 to 6 mm Hg over 24 to 48 hours.

The porcine heart valve prepared in this manner is then slowly dried under a vacuum and with the supply of temperature and thus completely dehydrated.

Thereafter, a plasma treatment of the porcine heart valve is carried out in a treatment chamber. For this purpose, the treatment chamber is completely evacuated and oxygen then introduced. A plasma is ignited by inputting a high-frequency electromagnetic field of, for example, 40 kHz or 13.56 MHz or by excitation with microwaves. The oxygen gas present in the treatment chamber is excited and radicalised by the energy supply connected therewith.

This plasma gas acts on the hydrocarbon groups $C_xH_y$ on the surface of the glutaraldehyde-fixed implant according to the following reaction equation:

$$C_xH_y + (x+y/4)O_2 \rightarrow xCO_2 + y/2H_2O.$$

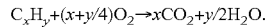

As can be seen, hydrocarbons on the implant surface, such as, for example, acetaldehydes are converted into the comparatively harmless chemical compounds carbon dioxide and water, which can be easily removed from the implant surface.

The above plasma treatment is then continued to apply the metal-containing coating on the implant surface. For this purpose, a gaseous precursor is fed into the coating chamber and is separated under the influence of the plasma energy into its atomic components. The ions thus being produced settle on the surface. Typically, titanium is primarily applied as the metal-containing coating with the aid of the PACVD method. The method as such is described in detail, moreover, in EP 0 897 997 B1 using the example of coating a plastics material substrate.

The reactor pressure both for the pre-treatment and for the coating is between 0.1 and 1030 mbar. When applying a plasma, the pressure should ideally be >50 mbar. For the pre-treatment, the working gas (for example oxygen) is introduced into the reactor at a gas volume flow of 0.04 Nl/min. After stabilisation of the end pressure to about 1 mbar, the capacitive plasma input takes place at a power of 20 W for a duration of 60 sec. The gas supply is then interrupted and the reactor chamber completely evacuated. The carrier gas (hydrogen) is guided for the following coating at a gas volume flow of 0.09 Nl/min over the precursor $Ti[N(CH_3)_2]_4$ and introduced into the coating chamber. The coating duration is about 300 sec. with an adjusted plasma power of 20 W. The gas supply is then stopped again and the coating chamber ventilated.

After this vacuum treatment for plasma loading and coating the porcine heart valves, these are again placed in liquid, so they regain their original consistency owing to the liquid supplied.

The invention claimed is:

1. A method for the treatment of biological tissue of animal or human origin so as to increase the biocompatibility, the method comprising:
   treating the tissue with an ionized plasma gas and coating the plasma treated tissue with a biocompatible, metal-containing coating selected from the group consisting of Ti, Ta, Nb, Zr, Hf, Ir, Au, Pd, Pt, Ag and Cu, said tissue being dried before the treatment by means of the plasma gas method, wherein the drying takes place by means of the influence of a vacuum and temperature.

2. The method according to claim 1, wherein nitrogen, hydrogen, argon or preferably oxygen is used as the ionized gas in a plasma gas method as the plasma treatment.

3. The method according to claim 2, wherein the energy input for the production of the plasma takes place by means of a high-frequency electromagnetic field, in particular a microwave field.

4. The method according to claim 1, wherein the plasma treatment takes place with an atmospheric plasma using a plasma jet under atmospheric conditions.

5. The method according to claim 1, wherein moisture is supplied to the dried tissue after the plasma treatment.

6. The method according to claim 1, wherein the metal-containing coating is applied by means of a Plasma Assisted Chemical Vapor Deposition (PACVD) method.

7. The method according to claim 1, wherein the tissue is selected from the group consisting of porcine heart valves, valves of bovine pericardium, or human cadaver heart valves.

8. The method according to claim 1, wherein said tissue is treated with glutaraldehyde prior to treating the tissue with said ionized plasma gas.

9. A method, comprising:
   providing an ionized plasma gas;
   providing a biological tissue;
   applying said ionized plasma gas to said biological tissue to form an ionized plasma treating tissue, the biological tissue being dried before applying the ionized plasma gas, wherein the drying takes place via a vacuum and temperature;
   applying a coating to said ionized plasma treating tissue, said coating comprising a biocompatible metal, said biocompatible metal being selected from the group consisting of Ti, Ta, Nb, Zr, Hf, Ir, Au, Pd, Pt, Ag and Cu.

10. The method according to claim 9, wherein the biological tissue is selected from the group consisting of porcine heart valves, valves of bovine pericardium, or human cadaver heart valves.

11. The method according to claim 9, wherein said tissue is treated with glutaraldehyde prior to treating the tissue with said ionized plasma gas.

12. The method according to claim 11, wherein the energy input for the production of the plasma takes place by means of a high-frequency electromagnetic field, in particular a microwave field.

13. The method according to claim 9, wherein the plasma treatment takes place with an atmospheric plasma using a plasma jet under atmospheric conditions.

14. The method according to claim 9, wherein moisture is supplied to the dried tissue after applying the ionized plasma gas.

* * * * *